US006682480B1

(12) United States Patent
Habib et al.

(10) Patent No.: US 6,682,480 B1
(45) Date of Patent: Jan. 27, 2004

(54) MONITORING TREATMENT USING IMPLANTABLE TELEMETRIC SENSORS

(75) Inventors: Nagy Adly Habib, London (GB); Alan John Sangster, Edinburgh (GB)

(73) Assignee: Imperial College Innovations Limited, London (GB)

( * ) Notice: Subject to any disclaimer, the term of this patent is extended or adjusted under 35 U.S.C. 154(b) by 0 days.

(21) Appl. No.: 09/744,220

(22) PCT Filed: Jul. 22, 1999

(86) PCT No.: PCT/GB99/02389

§ 371 (c)(1),
(2), (4) Date: Mar. 28, 2001

(87) PCT Pub. No.: WO00/04945

PCT Pub. Date: Feb. 3, 2000

(30) Foreign Application Priority Data

Jul. 22, 1998 (GB) .............................................. 9816011

(51) Int. Cl.⁷ ................................................. A61B 5/00
(52) U.S. Cl. ....................... 600/300; 600/301; 600/549; 600/561; 600/587
(58) Field of Search ................................... 600/300, 301, 600/316, 319, 323, 332, 339, 348, 361, 345, 364, 365, 347, 561, 587, 486; 128/903, 904, 897–899; 607/2, 60, 61

(56) References Cited

U.S. PATENT DOCUMENTS

| 3,852,755 A | 12/1974 | Works et al. |
| 4,075,632 A | 2/1978 | Baldwin et al. |
| 4,143,661 A | 3/1979 | LaForge et al. |
| 4,397,314 A | 8/1983 | Vaguine |
| 4,469,098 A | 9/1984 | Davi |
| 4,679,561 A | 7/1987 | Doss |
| 4,719,919 A | 1/1988 | Marchosky et al. |
| 4,825,880 A | 5/1989 | Stauffer et al. |
| 4,974,587 A | 12/1990 | Turner et al. |
| 5,190,541 A | 3/1993 | Abele et al. |
| 5,314,453 A | 5/1994 | Jeutter |
| 5,369,251 A | 11/1994 | King et al. |
| 5,370,675 A | 12/1994 | Edwards et al. |
| 5,472,441 A | 12/1995 | Edwards et al. |
| 5,500,012 A | 3/1996 | Brucker et al. |
| 5,582,588 A | 12/1996 | Sakurai et al. |
| 5,626,630 A | 5/1997 | Markowitz et al. |
| 5,629,678 A | 5/1997 | Gargano et al. |
| 5,704,352 A | 1/1998 | Tremblay et al. |
| 5,749,909 A | 5/1998 | Schroepel et al. |

(List continued on next page.)

FOREIGN PATENT DOCUMENTS

| DE | WO 95/07048 | 3/1995 | |
| FR | 0 073 709 A1 | 3/1983 | ............ A61N/5/04 |

OTHER PUBLICATIONS

J.O. McSpadden et al., "A Novel Oscillating Rectenna for Wireless Microwave Power Transmission", 1998 IEEE MTT–S Digest, pp. 1161–1163.

*Primary Examiner*—Charles Marmor
(74) *Attorney, Agent, or Firm*—Oppenheimer Wolff & Donnelly LLP

(57) ABSTRACT

Methods of and devices for monitoring the treatment of a human or non-human animal are disclosed. These involve a chip-sized passive sensor which is adapted (a) to receive and to rectify an electromagnetic signal with a frequency of 1–2 Ghz directed from outside the body towards it and to derive its operating power directly from the electromagnetic signal, and (b) to use its thus obtained operating power to transmit data relating to treatment by wireless telemetry to a receiver external to the body of the human or non-human animal. The data transmitted by the sensor is then processed to provide information on the treatment.

11 Claims, 3 Drawing Sheets

Schematic of Proposed Interstitial Microwave Array System

U.S. PATENT DOCUMENTS

| | | | |
|---|---|---|---|
| 5,830,139 A | * 11/1998 | Abreu | 600/399 |
| 5,833,603 A | 11/1998 | Kovacs et al. | |
| 5,963,132 A | 10/1999 | Yoakum | |
| 5,967,986 A | * 10/1999 | Cimochowski et al. | 600/454 |
| 5,978,713 A | * 11/1999 | Prutchi et al. | 607/60 |
| 6,015,386 A | 1/2000 | Kensey et al. | |
| 6,053,873 A | 4/2000 | Govari et al. | |
| 6,071,281 A | 6/2000 | Burnside et al. | |
| 6,123,701 A | 9/2000 | Nezhat | |
| 6,132,371 A | * 10/2000 | Dempsey et al. | 600/300 |
| 6,214,032 B1 | 4/2001 | Loeb et al. | |
| 6,231,516 B1 | * 5/2001 | Keilman et al. | 600/485 |
| 6,277,114 B1 | 8/2001 | Bullivant et al. | |
| 6,287,304 B1 | 9/2001 | Eggers et al. | |
| 6,443,952 B1 | 9/2002 | Mulier et al. | |

\* cited by examiner

SCHEMATIC OF PROPOSED 'WIRELESS' SYSTEM

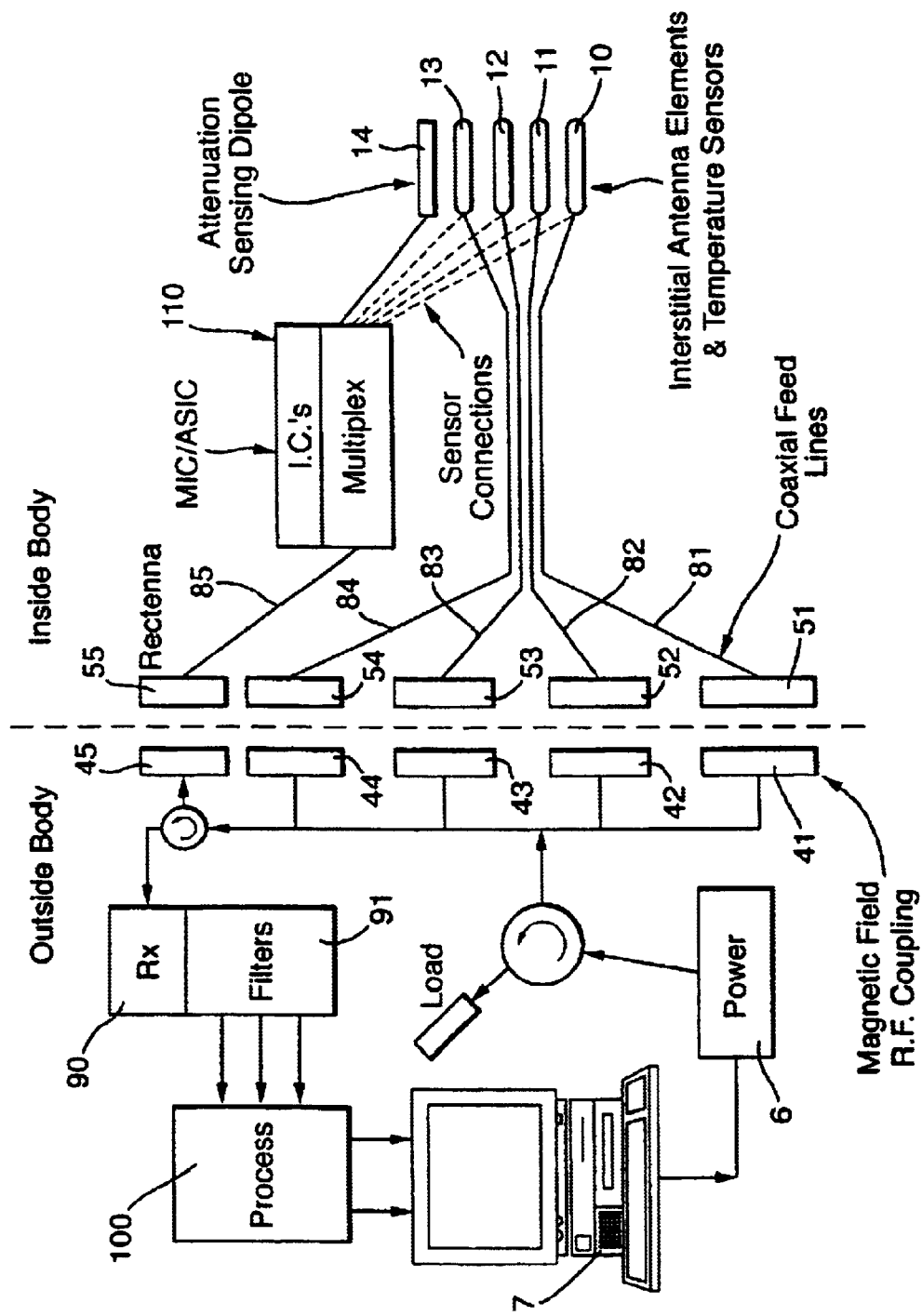

COLONIC STENT

PANCREATIC STENT

MONITORING TREATMENT USING IMPLANTABLE TELEMETRIC SENSORS

This invention relates to monitoring the treatment of human or non-human animals by means of implantable passive telemetric sensors. It is applicable to a variety of treatments but will be described hereinafter with particular reference to hyperthermia treatment, it being understood that the invention in not restricted to this type of treatment. Also, the induction will be described in relation to human patients, although it is to be understood that the monitoring involved may also be applied to non-human animals.

According to one aspect of the present invention, there is provided a method of monitoring the treatment of a human or non-human animal, which comprises implanting into the body of the human or non-human animal at or close to the desired locus of treatment a passive sensor which is adapted (a) to receive and to rectify an electromagnetic signal with a frequency of 1–2 GHz directed from outside the body towards the sensor so as to derive its operating power from maid electromagnetic signal, and (b) to transmit date relating to treatment parameters by wireless telemetry to a receiver external to the body of the human or non-human animal; and processing the data transmitted by said sensor to provide information on the treatment.

According to another aspect of the present invention, there is provided a device for implantation into the body of a human or non-human animal, which device comprises a passive sensor which is adapted (a) to receive and to rectify an electromagnetic signal with a frequency of 1–2 GHz directed from outside the body towards it and to derive its operating power from said electromagnetic signal, and (b) to transmit data relating to treatment parameters by wireless telemetry to a receiver external to the body of the human or non-human animal.

According do to a third a third aspect of the present invention, there is provided a system for monitoring the treatment of a human or non-human animal, which system comprises (a) a first component implanted into the body of the human or non-human animal at or close to the site of treatment; and (b) a second component in the form of a unit external to the body of the human or non-human animal, characterized in that:

(A) said first component comprises an antenna, rectification circuitry and signal processing circuitry;

(B) said second comprises is a microwave source, a receiver, a transmit/receive antenna and control circuitry for controlling the operation of the unit; and (C) said first component is arranged:
  (a) to receive and rectify an electromagnetic signal with a frequency of 1–2 GHz transmitted by the antenna of said second component and to derive its operating power from said electromagnetic signal, and
  (b) to transmit data relating to treatment parameters by wireless telemetry to said second component; and (D) said second component is arranged to transmit an electromagnetic signal with a frequency of 1–2 GHz towards said first component and to interrogate said first component to derive therefrom data pertaining to the treatment which human or non-human animal is undergoing.

In one particular embodiment of the invention, the sensor is a miniature pressure sensor; this may, for example, be associated with a stent whose function is to maintain the lumen patency of a duct, vessel or organ. Such devices may be employed at many sites within the body and may provide valuable information during the treatment of a wide range of conditions. The sensor may, for example, be incorporated in a transjugular intrahepatic portosystemic shunt (TIPS) or in a stent within the renal artery.

The desired locus of treatment may be, for example, a tumour; a blood vessel (for example, where levels of circulating species, or general flow rates, are to be monitored); or a duct, e.g. the pancreatic duct or bile duct. Many other loci exist and will naturally be determined according to the needs of the patient.

preferably, the sensor is associated with a therapeutic device which is also implanted into the human or non-human animal body in the method of this invention. Non-limiting examples of the implanted therapeutic device include:

- a device for delivering heat in a localised manner, e.g. to treat a tumour;
- pump for assisting blood flow;
- a stent for ensuring lumen patency of hollow viscera and ducts, e.g. oesophagus, bile duct, pancreatic duct, colon, stomach, rectum and urethra;
- a pressure sensor for detecting localised pressures, e.g. within a stent of the type just mentioned;
- a flow meter for determining passage of a fluid through a duct;
- a drug release device;
- a pacemaker;
- a detector for particular chemical or biological material or species, e.g. blood or tissue chemical content or cellular content;
- or combinations of such devices.

Localised heating can be of benefit in several situations, for example: (a) to stop bleeding, e.g. of a tumour or in a non-malignant condition such as benign ulcers of the stomach or duodenum. The therapeutic device may thus be an electrode or an assembly of electrodes which can be activated (preferably remotely) so as to generate localised heating of adjacent tissues. An electrode of this sort may, for example, be positioned around a tumour of the prostate, colon, bladder, stomach or lung; it may likewise be positioned adjacent to a duodenal or stomach ulcer.

The invention also finds application in surgical procedures involving balloon dilatation and/or coronary stenting. These surgical procedures tend to encourage the formation of fibrous tissue which can lead to stenosis, e.g. blockage of a blood vessel after removal of the dilatation equipment. In accordance with this invention, such dangers of stenosis may be removed or mitigated by heating the stent during a coronary stenting procedure or by applying heat adjacent to a region undergoing balloon dilatation. Control of the heating process is assisted by sensing the temperature of the heated component.

The sensor associated with the therapeutic device will be configured to respond to a parameter (e.g. temperature, flow rate, pressure) which is of significance in the treatment regime being followed. Thus in the treatment of a tumour by hyperthermia, the parameter sensed may be temperature; and in the treatment of an occluded duct, the parameter sensed may be pressure.

The transmission of data from within the body to an external receiver may be accomplished using low power radiation in the radio frequency or microwave frequency bands. Such transmission is preferably intermittent rather than continuous and will generally be under the control of medical personnel or, in the case of a human patient of the patient him/herself.

Advantageously, the sensor (and the therapeutic device also, if this requires electrical power to operate is/are empowered by wireless means. While in some instances batteries may be implanted as a power source, this is not preferred; the currently preferred mode of delivery is by means of an implanted antenna/rectifier device (a so-called "rectenna") which receives electromagnetic radiation from an external source and delivers electrical power derived therefrom. Typically, the power levels involved for sensor applications are less than about 1 mW; at these levels, the antenna portion of the rectenna can be implemented as a filamentary coil-shaped antenna for low frequencies or as a short dipole antenna for high frequencies. A chip-sized (typically less than 1 mm$^3$) rectifying circuit comprising a combination of rectifying diodes, a storage capacitor and (optionally) a filter circuit is mounted on the antenna. Typically, the sensor/rectenna combination occupies a volume of around 60 mm$^3$ or less.

Electromagnetic radiation at a frequency of 1–2 GHz and with a power density of 1 mW/cm$^2$ will provide such a rectenna with adequate operating power. This may advantageously be provided by an external transmit/receive unit which will direct electromagnetic radiation towards the implanted rectenna in order to power up and interrogate the sensor electronics. Such a unit will operate in a duplex fashion, simultaneously transmitting the power signal to the implanted unit(s) and receiving the telemetry signal containing the data required from the unit(s).

To maximise the efficiency of the power delivery system, it may be advantageous to use polarised electromagnetic radiation and a correspondingly configured rectenna.

There exist many circumstances within the human or non-human body where regular measurement of parameters of body function would provide information important for the management of a variety of disorders. For example, those tumours which generate marker substances could easily be monitored by an implanted sensor in accordance with this invention. Monitoring of acute phase protein, and particularly of reactive c-phase protein, is commonly undertaken in many patients through the technique of venesection. Similarly, patients suffering from chemical imbalances (e.g. hormonal imbalance) could use an implanted sensor in accordance with this invention to determine their hormonal status as and when required. For example, in patients suffering from thyroid deficiency, a thyroxin detector could be used to determine circulating levels of thyroid. Certain cardiovascular and immunological problems have very specific blood-borne indicators of condition which may be monitored by means of the present invention. Such applications as mentioned above fall within the scope of this invention. Equally, the sensor may be used to monitor pharmacokinetics, e.g. when chronic administration of drugs (e.g. digoxin or tamoxifen) is required.

For a better understanding of the invention, and to show how the same may be carried into effect, reference will now be made, by way of example, to the accompanying drawings, which illustrate an embodiment of the invention applied to a therapeutic system for hyperthermia treatment of a liver tumour, and in which:

FIG. 2 shows more detail of the disposition of implanted components and their operation in hyperthermia treatment of a patient.

Figure 1:
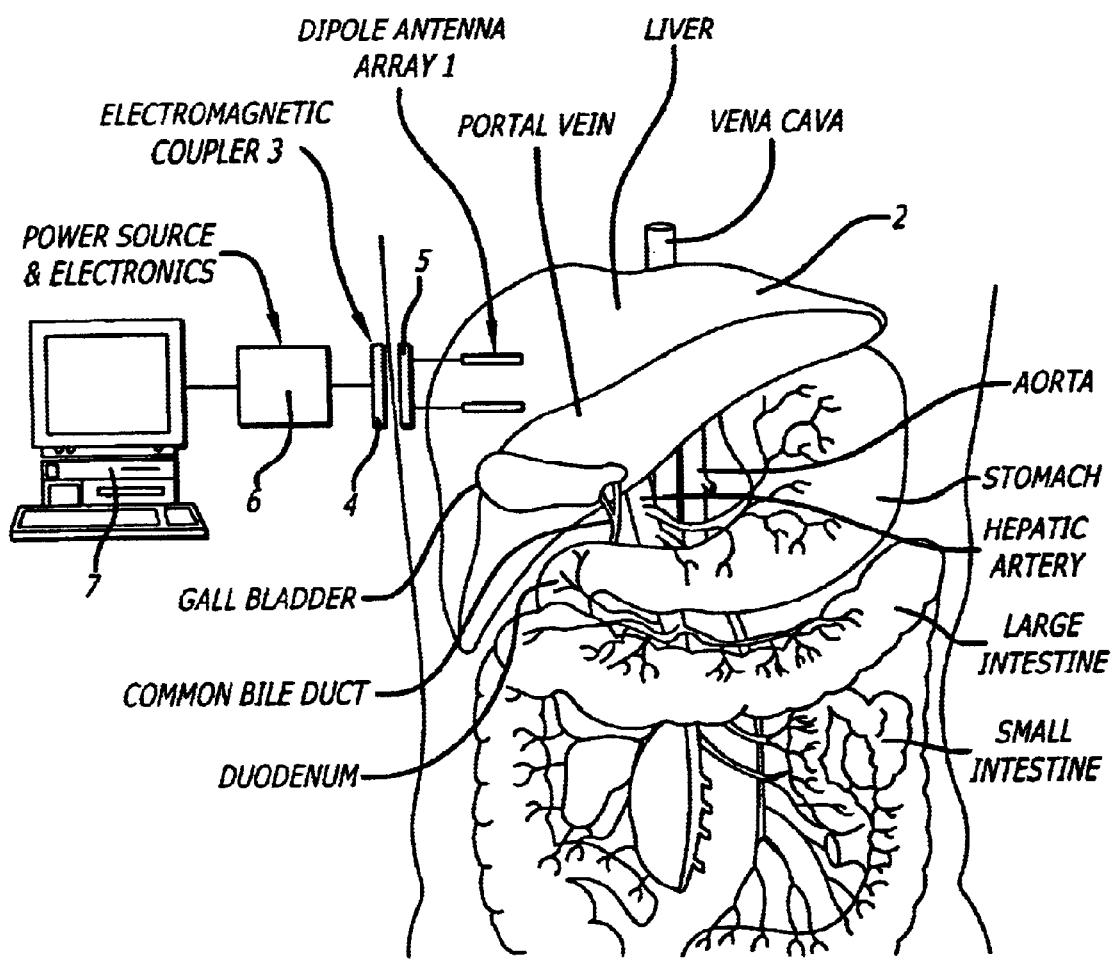
FIG. 1 illustrates schematically the basic sensor interrogation system of this invention.

Referring to FIG. 1, one or more sensor chips 1 are implanted into the malignant region of a patient's liver. Each sensor chip comprises three basic elements, namely a rectenna 3, electronic processing circuitry 4 in the form of an integrated circuit, and a sensing device 5. An antenna 7 (see FIG. 2) is part of the rectenna 3. A sensor chip incorporating these components may be no more than 10 mm long, 2 mm wide and 1 mm thick. To activate the sensor chip, a reader/interrogator 6 is used to irradiate the sensor chip(s) with a radio signal which is of sufficient power to enable the rectenna 3 to generate a voltage large enough to cause the electromagnetic component 4 of the sensor to function. The reader unit 6 will normally be located just outside, and close to, the body of the patient; it may for example be hand-held; attached to a belt around the patient's body; or otherwise located in a substantially fixed position relative to the body.

Referring to FIG. 2, a practical implementation of the reader/interrogation unit 6 of FIG. 1 is shown. A source 11 of radio waves (typically in the frequency range 1000 MHz–2000 MHz) foods a directional antenna 12 through a circulator 13. The transmit source 11 may be modulated under control of an integrated circuit 14 which provides sign coding and processing capabilities. The unit further comprises a receiver 15 which receives signals transmitted telemetrically by the implanted sensor and which supplies the received signals to the integrated circuit 14 which is adapted to decipher coded transmissions from the sensor chip 1. A display screen 16 is also provided in the unit 6 for the purpose of displaying the information received from within the patient.

By means of a system as just described, it may be possible to provide relatively simple, auto-regulated control of tumours which, because of their siting or their characteristics or the previous treatment history of the patient are not susceptible to conventional methods of treatment.

The system as described may be used in conjunction with secondary techniques, for example the direct injection of paracrine hormones or of cells secreting paracrine hormones. These are believed to promote apoptosis of tumours and/or to encourage infiltration of the heated tumour by cells of the innate immune system.

In designing the components for implantation in the present invention, it is desirable to minimise the size of the components to reduce tissue damage during the implantation step; to maximise their rigidity to increase the accuracy with which they can be positioned within the body of a patient; and to encapsulate the components in non-toxic, non-reactive material. Further, the control system employed preferably allows different modes of activation of the antenna elements 10–13 so as to permit variation of the spatio-temporal heat delivery.

Figure 3A:
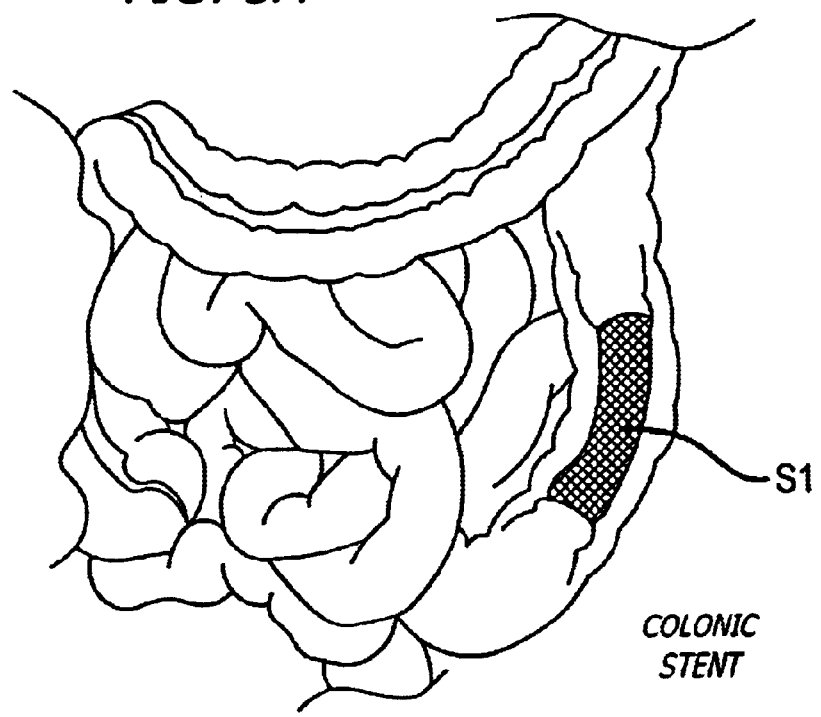
FIGS. 3A and 3B illustrate stents implanted, respectively, in the colon and in the pancreatic duct.
Figure 3B:
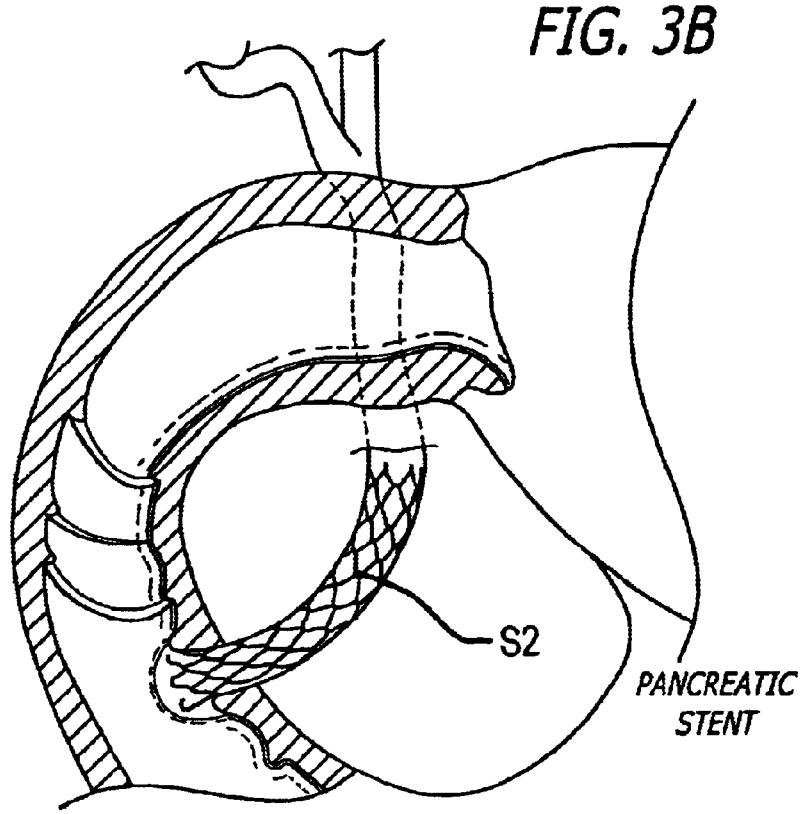

FIGS. 3A and 3B show metallic or metal-containing stents $S_1$ and $S_2$, respectively, in the human colon and pancreatic duct. These serve to maintain the lumen patency of the organs or ducts in which they are implanted, and where partial or complete occlusion (e.g. by a tumour) has occurred. By implanting coupling elements and a rectenna in operative connection with the stent, heat may be delivered to kill the tumour calls. As illustrated in FIG. 2, control and monitoring means may be incorporated to provide telemetric control and operation of the hyperthermia treatment.

What is claimed is:

1. A device for implantation into the body of a human or non-human animal, which device comprises a chip sized passive sensor which is adapted (a) to receive and to rectify an electromagnetic signal with a frequency of 1–2 GHz directed from outside the body towards said sensor, the sensor being adapted to derive its operating power directly from said electromagnetic signal, and (b) to use power thus obtained by said sensor to transmit data relating to treatment parameters by wireless telemetry to a receiver external to the body of the human or non-human animal in response to the received electromagnetic signal with a frequency of 1–2 Ghz.

2. A device as claimed in claim 1, which is adapted to remain inactive and not consuming any power unless said sensor is activated by an external radio signal.

3. A device as claimed in claim 1, wherein the device includes an antenna/rectifier to provide operating power from incoming electromagnetic energy.

4. A device as claimed in claim 3, wherein said antenna/rectifier is adapted to provide operating power from incoming polarized electromagnetic energy.

5. A device as claimed in claim 1, wherein said sensor is a pressure sensor.

6. A device as claimed in claim 1, which further comprises a therapeutic device.

7. A device as claimed in claim 6 wherein said therapeutic device is one or more of:

(1) a device for delivering heat in a localized manner, (2) a pump for assisting blood flow;

(3) a stent for ensuring lumen patency of hollow viscera and ducts;

(4) a pressure sensor for detecting localized pressures;

(5) a flow meter for determining passage of a fluid through a duct;

(6) a drug release device;

(7) a pacemaker; and (8) a detector for particular chemical or biological material or species.

8. A device as claimed in claim 6, wherein said therapeutic device is a device for delivering heat in a localized manner in order to treat a tumor.

9. A method of monitoring treatment of a human or non-human animal, which comprises implanting into the body of the human or non-human animal at or close to a desired locus of treatment a chip size passive sensor which is adapted (a) to receive and to rectify an electromagnetic signal with a frequency of 1–2 GHz directed from outside the body towards the sensor, with the said sensor deriving its operating power directly from said electromagnetic signal, and (b) to use power thus obtained by said sensor to transmit data relating to treatment parameters by wireless telemetry to a receiver external to the body of the human or non-human animal in response to the received electromagnetic signal with a frequency of 1–2 Ghz; and processing the data transmitted by said sensor to provide information on the treatment.

10. A system for monitoring the treatment of a human or non-human animal, which system comprises (a) a first component adapted to be implanted into the body of the human or non-human animal at or close to a site of treatment; and (b) a second component in the form of a unit external to the body of the human or non-human animal, wherein:

(A) said first component is chip sized, comprises rectification circuitry and signal processing circuitry and is attached to an antenna;

(B) said second component comprises a microwave source, a receiver, a transmit/receive antenna and control circuitry for controlling wireless interrogation of said first component; and (C) said first component is arranged:

(a) to receive and rectify an electromagnetic signal with a frequency of 1–2 GHz transmitted by the antenna of said second component, said first component being adapted to utilize the rectified signal strength to power active device within said first component and (b) to transmit data relating to treatment parameters by wireless telemetry to said second component in response to the received electromagnetic signal with a frequency of 1–2 Ghz; and (D) said second component is adapted to transmit an electromagnetic signal with a frequency of 1–2 GHz towards said first component and, using operating power derived from said electromagnetic signal when said first component is in use in the body of the human or non-human animal, to interrogate said first component to derive therefrom data pertaining to the treatment which the human or non-human animal is undergoing.

11. A system as claimed in claim 8, wherein the antenna of the first component is a filamentary coil shaped antenna.

* * * * *